(12) United States Patent
Bernard et al.

(10) Patent No.: US 6,912,417 B1
(45) Date of Patent: Jun. 28, 2005

(54) METHOD AND APPARATUS FOR DELIVERY OF THERAPEUTIC AGENTS

(75) Inventors: Robert M. Bernard, Rancho Santa Fe, CA (US); Andrew W. Hannaman, San Diego, CA (US); Brady M. Bernard, Rancho Santa Fe, CA (US)

(73) Assignee: Ichor Medical Systmes, Inc., San Diego, CA (US)

( * ) Notice: Subject to any disclaimer, the term of this patent is extended or adjusted under 35 U.S.C. 154(b) by 149 days.

(21) Appl. No.: 10/117,457

(22) Filed: Apr. 5, 2002

(51) Int. Cl.[7] .................................................. A61N 1/30
(52) U.S. Cl. ..................................... 604/20; 435/173.6
(58) Field of Search ........................ 604/890.1, 891.1, 604/68–72, 131, 134–137, 140, 141, 143–147, 604/149–157, 20, 21, 205, 187, 501; 435/173.5–173.7; 204/450; 607/115, 116, 120

(56) References Cited

U.S. PATENT DOCUMENTS

| | | | | |
|---|---|---|---|---|
| 4,394,863 A | * | 7/1983 | Bartner | 604/90 |
| 4,832,682 A | * | 5/1989 | Sarnoff | 604/21 |
| 5,273,525 A | * | 12/1993 | Hofmann | 604/21 |
| 5,306,236 A | * | 4/1994 | Blumenfeld et al. | 604/21 |
| 5,383,851 A | * | 1/1995 | McKinnon et al. | 604/68 |
| 5,593,429 A | * | 1/1997 | Ruff | 607/116 |
| 5,702,359 A | * | 12/1997 | Hofmann et al. | 604/20 |
| 6,278,895 B1 | * | 8/2001 | Bernard | 604/20 |
| 6,356,783 B1 | * | 3/2002 | Hubbard, Jr. | 600/546 |
| 6,516,223 B2 | * | 2/2003 | Hofmann | 604/21 |
| 6,520,950 B1 | * | 2/2003 | Hofmann et al. | 604/503 |
| 6,558,351 B1 | * | 5/2003 | Steil et al. | 604/131 |

* cited by examiner

Primary Examiner—Nicholas D. Lucchesi
Assistant Examiner—Catherine S. Williams
(74) Attorney, Agent, or Firm—James C. Weseman, Esq.; The Law Offices of James C. Weseman

(57) ABSTRACT

Methods and apparatus for the reproducible, consistent and efficacious delivery of a therapeutic agent to a patient. The invention comprises means for the controlled administration of the therapeutic agent through an orifice to the patient, a plurality of penetrating electrodes arranged with a predetermined spatial relationship relative to the orifice, and means for generating an electrical signal operatively connected to the electrodes.

20 Claims, 7 Drawing Sheets

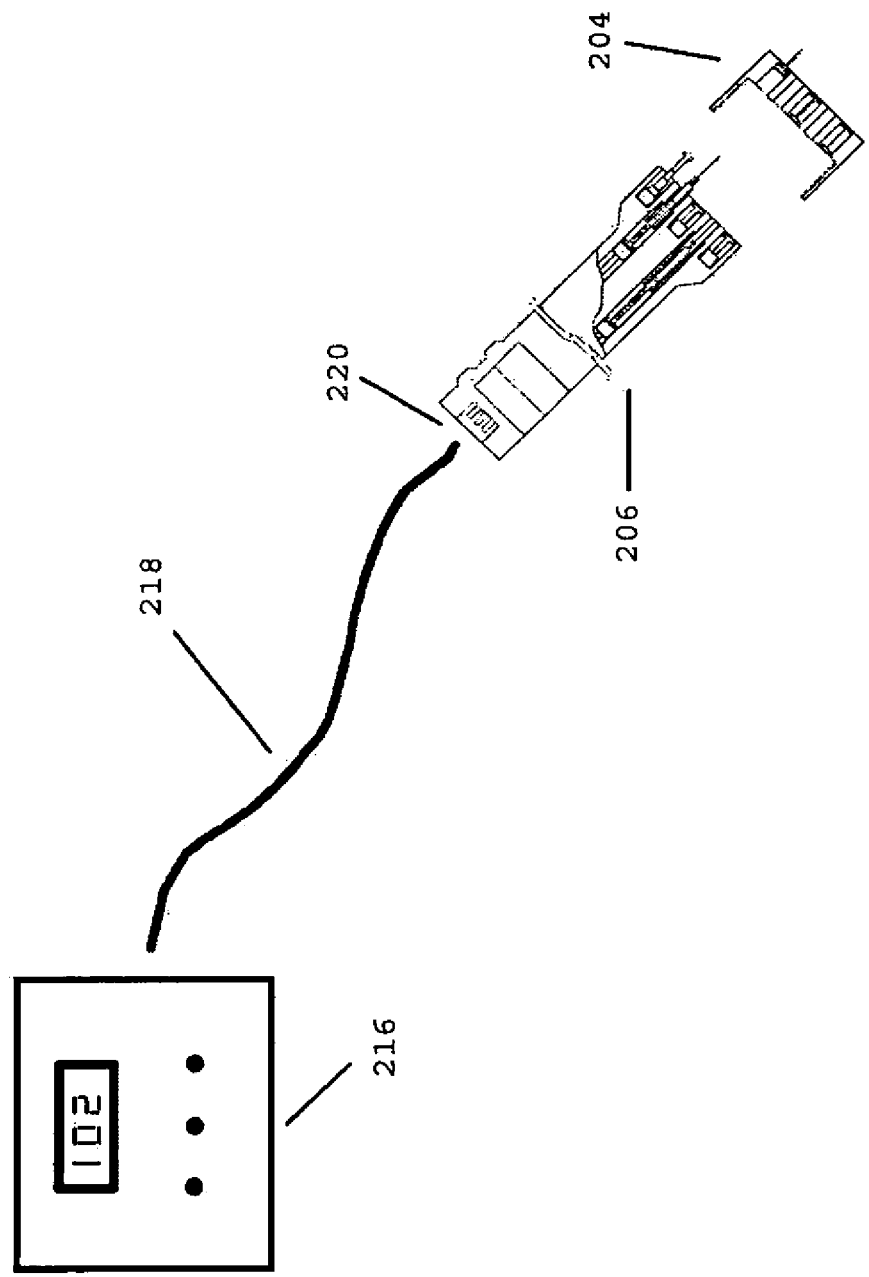

METHOD AND APPARATUS FOR DELIVERY OF THERAPEUTIC AGENTS

TECHNICAL FIELD

The present invention is directed to the delivery of prophylactic and therapeutic agents to patients and, more particularly, to the reproducible, consistent, and efficacious delivery of prophylactic and therapeutic agents, such as nucleic acids, drugs, and proteins, to defined regions in selected tissues of interest.

BACKGROUND OF THE INVENTION

Prophylactic and therapeutic agents have long been delivered to patients using various conventional routes of administration, such as topical, oral, intravenous, parenteral, and the like. Once administered to the patient by the selected route, the delivery of the agent to the tissue of interest and its beneficial interaction with the tissue is largely dependent on its inherent physicochemical factors, but may have been facilitated by, for example, selected components of the delivery composition such as carriers, adjuvants, buffers and excipients, and the like.

More recently, the application of electrical signals has been shown to enhance the movement and uptake of macromolecules in living tissue. Application of such electrical signals in tissue relative to the administration of a prophylactic or therapeutic agent can have desirable effects on the tissue and/or the agent to be delivered. Specifically, techniques such as electroporation and iontophoresis have been utilized to significantly improve the delivery and/or uptake of a variety of agents in tissue. Such agents include pharmaceuticals, proteins, and nucleic acids. Potential clinical applications of such techniques include the delivery of chemotherapeutic drugs and/or therapeutic genes in tumors, the delivery of DNA vaccines for prophylactic and therapeutic immunization, and the delivery of nucleic acid sequences encoding therapeutic proteins.

Many devices have been described for the application of electrical signals in tissue for the purpose of enhancing agent delivery. The vast majority of these have focused on a means for effective application of the electrical signals within a target region of tissue. A variety of surface and penetrating electrode systems have been developed for generating the desired electrophysiological effects.

In spite of the promise associated with electrically mediated agent delivery and the potential clinical applications of these techniques, progress has been hampered by the lack of an effective means to achieve the overall objective of efficient and reliable agent delivery using these techniques. One of the most significant shortcomings of current systems is the inability to achieve reliable and consistent application from subject to subject. Significant sources of this variability are due to differences in the technique and skill level of the operator. Other sources of variability that are not addressed by current systems include differences in the physiologic characteristics between patients that can affect the application of the procedure.

Given that reliable and consistent application of clinical therapies is highly desirable, the development of improved application systems is well warranted. Such development should include a means for minimizing operator-associated variability while providing a means to accommodate the differences in patient characteristics likely to be encountered during widespread clinical application of electrically mediated agent delivery.

DISCLOSURE OF THE INVENTION

The present invention provides improved methods and apparatus for the reproducible, consistent, and efficacious delivery of therapeutic agents, such as nucleic acids, drugs, and proteins, to patients utilizing Electrically Mediated Therapeutic Agent Delivery.

In one aspect, the present invention provides an apparatus for the delivery of a therapeutic agent to a predetermined site within a patient comprising means for the controlled administration of the therapeutic agent to the patient comprising a reservoir for the therapeutic agent, at least one orifice through which the agent is administered, and a controlled source of energy sufficient to transfer a predetermined amount of the therapeutic agent at a predetermined rate from the reservoir through the orifice to the predetermined site within the patient. In addition, the apparatus comprises a plurality of penetrating electrodes arranged with a predetermined spatial relationship relative to the orifice, and means for generating an electrical signal operatively connected to the electrodes.

Other aspects of the invention include methods comprising Therapeutic Agent Administration in controlled spatial and temporal conjunction with Electric Signal Administration.

BRIEF DESCRIPTION OF THE DRAWINGS

FIG. 7 is a block diagram of a treatment system in accordance with the invention.

DETAILED DESCRIPTION OF THE INVENTION

Figure 1:
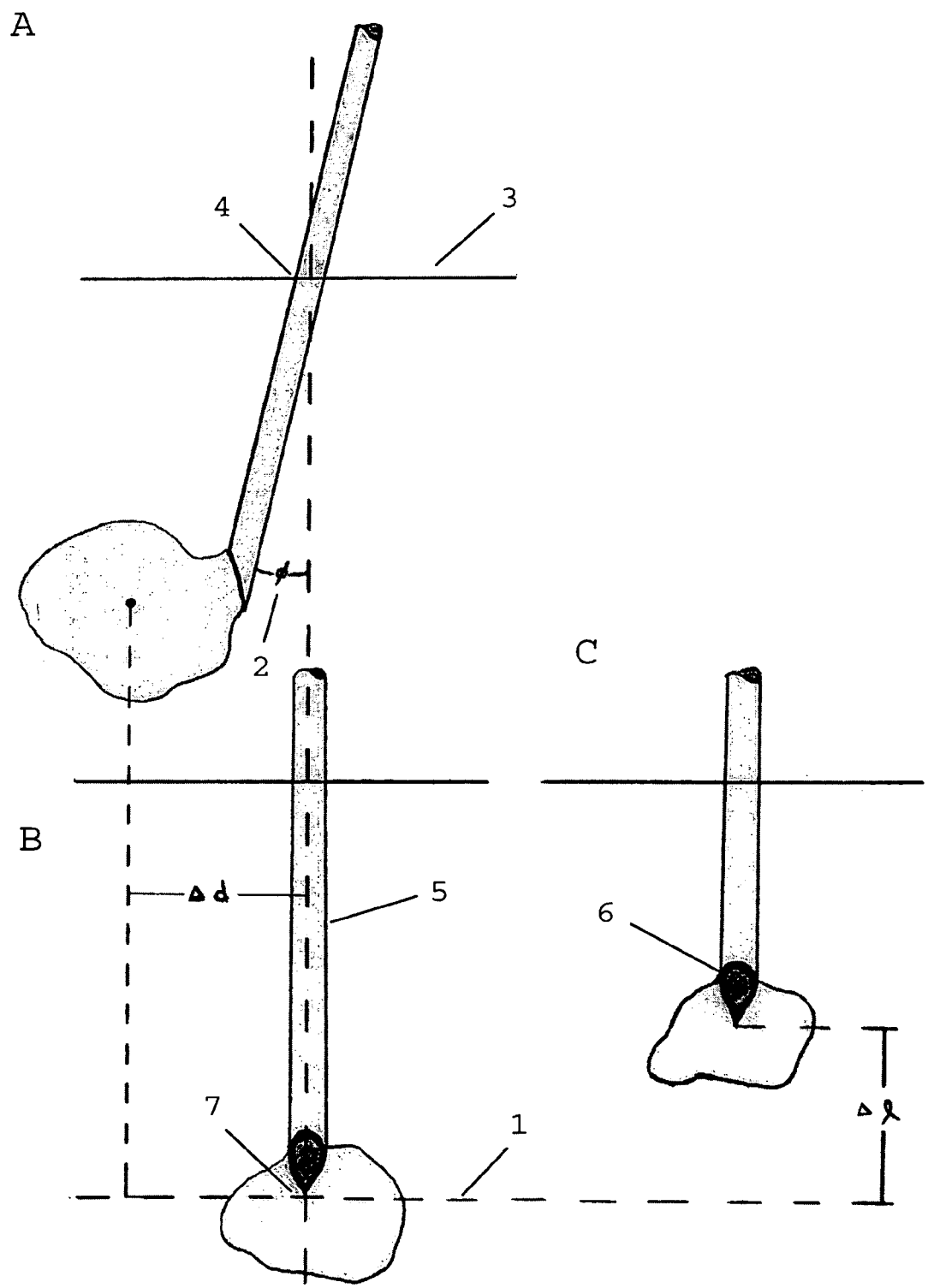
FIGS. 1A–C are graphic depictions of potential sources of spatial variability associated with conventional needle syringe injection.

The present invention provides improved methods and apparatus for the reproducible, consistent, and efficacious delivery of therapeutic agents, such as nucleic acids, drugs, and proteins, with Electrically Mediated Therapeutic Agent Delivery (EMTAD).

In one aspect, the present invention provides an apparatus for the delivery of a therapeutic agent to a predetermined site within a patient comprising means for the controlled administration of the therapeutic agent to the patient comprising a reservoir for the therapeutic agent, at least one orifice through which the agent is administered, and a controlled source of energy sufficient to transfer a predetermined amount of the therapeutic agent at a predetermined rate from the reservoir through the orifice to the predetermined site within the patient. In addition, the apparatus comprises a plurality of penetrating electrodes arranged with a predetermined spatial relationship relative to the orifice, and means for generating an electrical signal operatively connected to the electrodes.

In the present invention, EMTAD is defined as the application of electrical signals to biological tissue for the purpose of enhancing movement and/or uptake of a therapeutic agent in tissue. The process of EMTAD is comprised of two elements: 1) Therapeutic Agent Administration (TAA), and 2) an Electrical Signal Application (ESA) sufficient to induce the desired EMTAD effect. In the present invention, therapeutic agent administration is accomplished in a controllable fashion, termed Controlled Therapeutic Agent Administration (CTAA). The term CTAA used herein refers to methods and apparatus capable of providing spatial and temporal control over administration of a therapeutic agent relative to the induction of an EMTAD effect. Controllable administration techniques may utilize variations on the conventional needle-syringe (e.g. automatic injection device) and/or various needleless methodologies (e.g. jet injector, transdermal/transcutaneous patch, oral, gel, cream, or inhaled administration). The term ESA used herein refers to the application of electrical signals to facilitate or enhance the delivery of therapeutic agents by improving movement and/or uptake of said agents within tissue, thus inducing an EMTAD effect. When used to facilitate or enhance delivery of a therapeutic agent, ESA processes such as electroporation, iontophoresis, electroosmosis, electropermeabilization, electrostimulation, electromigration, and electroconvection all represent various modes of EMTAD.

Specific applications for EMTAD include, but are not limited to, the delivery of vaccines, therapeutic proteins, and chemotherapeutic drugs. Traditionally with such applications, EMTAD is initiated by therapeutic agent injection using a conventional needle-syringe. After the agent has been administered, a device suitable for ESA is applied to the patient at a designated location. Finally, an appropriate ESA protocol is utilized to provide the desired facilitation or enhancement to therapeutic agent delivery. With traditional EMTAD, however, the desired spatial and temporal relationship between agent administration and ESA may not be realized.

Spatial Parameters

For agents in which the use of EMTAD is not required or desirable, therapeutic agent administration is often performed using a conventional needle syringe. While the therapeutic objectives can usually be accomplished using these means, the need to deliver certain agents with EMTAD brings an additional level of complexity to the issue of TAA. As depicted in FIG. 1, in any conventional needle-syringe injection, as the needle 5 is inserted into the tissue, the depth 1 and the angle 2 of insertion relative to the surface of the tissue 3 can be difficult to control. Additionally, the point of needle penetration 4 at the tissue surface 3 may not be representative of the location of the orifice 6 and the region of agent administration 7 within the target tissue. As an illustrative example a transcutaneous intramuscular injection may not correspond to the site of insertion on the skin since the two tissues can often move in relation to one another.

While this conventional approach is generally adequate for the delivery of many different therapeutics that do not require EMTAD, these variables lead to a distribution of the therapeutic agent following injection that is often inconsistent and/or indeterminate and can hamper effective EMTAD. Commonly, the most effective use of EMTAD utilizes a predefined relationship between the therapeutic agent and ESA within the patient. As a result, the lack of spatial control over TAA in a target tissue using a conventional needle syringe can hamper the outcome of the EMTAD application. One illustrative example of this concept is the use of electroporation to facilitate the delivery of a therapeutic agent. Electroporation is typically most effective in enhancing therapeutic agent delivery when TAA and ESA are co-localized within the target region of tissue. In many cases, if the agent to be delivered and the induced electroporation effect are not co-localized within the target region of tissue, the delivery of said agent is suboptimal.

Another example of the need for adequate spatial control of TAA in EMTAD is iontophoresis. This mode of EMTAD uses electrical fields to cause movement of charged molecules. In order to achieve the desired movement of the agent, the proper spatial relationship between the electrodes and the therapeutic agent must be realized. If a negatively charged agent were placed in close proximity to the location of a positive electrode, little or no movement of the agent through the tissue would be observed. In contrast, localization of the said negatively charged agent near the negative electrode would result in significant movement of the agent through the tissue in the direction of the positive electrode.

As illustrated by the preceding examples, care must be taken to control the precise location of TAA relative to the application of ESA to achieve the desired effect. As a result, methods for achieving reproducible, consistent, and well-characterized distribution of the therapeutic agents are highly desirable.

Temporal Parameters

Another disadvantage with conventional needle-syringe injection TAA is that the rate of injection may vary from one operator to another, thereby causing inconsistent agent distribution in the tissue. Additional temporal variability is introduced when multiple device placements are required to complete the EMTAD process. For example, one application of EMTAD calls for the administration of plasmid DNA encoding for a therapeutic protein, followed by generation of an electroporation-inducing electrical field. Using the traditional method of EMTAD, the plasmid is injected with a needle-syringe, followed by placement and activation of the electroporation device. By requiring two separate device placements (the initial needle syringe followed by the ESA device), this procedure is susceptible to inter-patient variability arising from inconsistent temporal application of each device by the operator. Additionally, the use of two separate device placements leads to an unavoidable time interval in between the clinician's placement and activation of each device. This is compounded in the case where multiple application sites are necessary to achieve adequate delivery of the agent to a specifiable region within the target tissue.

These issues are especially critical for agents, such as nucleic acids, that can be degraded or inactivated in the extracellular environment. Therapeutic agent degradation can lead to a reduction in efficacy and consistency in the application of the therapy. Also, the inter-patient rate of therapeutic agent degradation is not constant, thus contributing to the overall therapeutic inconsistency of conventional needle-syringe injection combined with ESA, and more specifically with electroporation therapy.

Due to the inherent difficulty of spatial and temporal variability with conventional needle-syringe injection used in conjunction with ESA, the precise location and timing of TAA relative to ESA is often unknown. As a result, the effective administration and dosing of therapeutic agents with EMTAD may be inconsistent and irreproducible. Though conventional needle-syringe injection is sometimes adequate for therapeutic agent administration, reproducible and consistent agent delivery is significantly enhanced by controlling the spatial and temporal relationship between administration of the therapeutic agent and induction of the desired EMTAD effect.

Thus, while the traditional EMTAD procedure may be adequate for certain applications, temporal and spatial control is highly desirable for clinical applications that typically require a high degree of consistency and reproducibility. In contrast to the conventional EMTAD approach previously described, several techniques for combined CTAA and ESA are described herein to provide more advantageous methods and apparatus for the clinical application of EMTAD. The present invention utilizes various aspects of CTAA in conjunction with ESA to provide reproducible, consistent, and efficacious therapeutic agent delivery. More specifically, this invention describes methods and apparatus to provide spatial and temporal control over administration of a therapeutic agent relative to the application of electrical signals, thereby improving the movement and/or uptake of said agent in the target tissue.

In the present invention, there exists a controllable spatial relationship for the administration of the therapeutic agent relative to the application of electrical signals. Prior to treatment, the optimal location for TAA relative to ESA is determined. This spatial relationship between TAA and ESA is dictated by treatment parameters, including the nature of the agent being administered and the properties of the target tissue to which the agent is administered. In certain applications, electrical signals are preferentially applied distal to the site of therapeutic agent administration. However, the typical spatial relationship is to apply the EMTAD-inducing electrical signals proximal to the site of agent administration. In the practice of such applications, co-localization between TAA and ESA may be preferential. This is often the case when electroporation and/or iontophoresis are utilized for induction of the desired EMTAD effect.

Another aspect of the invention provides a controllable temporal relationship for the sequence and timing of TAA relative to ESA. Prior to treatment, the optimal sequence and timing for combination of TAA and ESA is determined. As with the spatial relationship, the desired temporal relationship between TAA and ESA is dictated by parameters such as the nature of the agent being administered and the properties of the target tissue to which the agent is administered. In certain applications, exposure to the electrical fields associated with ESA may adversely affect the therapeutic agent. In the practice of such applications, generation of such electrical fields is followed by CTAA. However, the typical temporal relationship is CTAA followed by ESA.

The present invention provides improved methods and apparatus for the reproducible, consistent, and efficacious delivery of therapeutic agents, such as nucleic acid based constructs, pharmaceutical compounds, drugs, and proteins, with EMTAD. This objective is accomplished by controlling the spatial and temporal administration of a therapeutic agent relative to application of electrical signals. Specific applications for EMTAD include, but are not limited to, the delivery of vaccines, therapeutic proteins, and chemotherapeutic drugs. Traditionally with such applications, EMTAD is initiated by therapeutic agent injection using a conventional needle-syringe. After the agent has been administered, a device suitable for ESA is applied to the patient at a designated location. Finally, an appropriate ESA protocol is utilized to provide the desired facilitation or enhancement to therapeutic agent delivery. One such ESA method that has proven to be effective in virtually all cell types is electroporation. Other methods of electrically mediated delivery include iontophoresis, electroosmosis, electropermeabilization, electrostimulation, electromigration, and electroconvection. These terms are used for illustrative purposes only and should not be construed as limitations in the invention.

The technique of electroporation utilizes the application of electric fields to induce a transient increase in cell membrane permeability and to move charged particles. By permeabilizing the cell membranes within the target tissue, electroporation dramatically improves the intracellular uptake of exogenous substances that have been administered to the target tissue. The increase in cell membrane permeability and molecular movement due to electroporation offers a method for overcoming the cell membrane as a barrier to therapeutic agent delivery. The application of electroporation as a technique for inducing EMTAD is advantageous in that the physical nature of the technique allows electroporation to be applied in virtually all tissue types. Accordingly, various aspects and embodiments of the invention discuss, but are not limited to, electroporation as a technique for inducing EMTAD.

Therapeutic Agents

The term "therapeutic agent" will be used in its broadest sense to include any agent capable of providing a desired or beneficial effect on living tissue. Thus, the term will include both prophylactic and therapeutic agents, as well as any other category of agent having such desired effects. Clearly, the scope of the present invention is sufficiently broad to include the controlled delivery of any agent, however categorized. Therapeutic agents include, but are not limited to pharmaceutical drugs and vaccines, and nucleic acid sequences (such as supercoiled, relaxed, and linear plasmid DNA, antisense constructs, artificial chromosomes, or any other nucleic acid-based therapeutic), and any formulations thereof. Such agent formulations include, but are not limited to, cationic lipids, cationic polymers, liposomes, saline, nuclease inhibitors, anesthetics, poloxamers, preservatives, sodium phosphate solutions, or other compounds that can improve the administration, stability, and/or effect of the therapeutic agent. Additional benefits derived from certain agent formulations include the ability to control viscosity and electrical impedance of the administered agent, an important consideration for EMTAD applications.

In the case of nucleic acids, an example of a therapeutic agent would be plasmid DNA dissolved in a sodium phosphate solution with a competitive nuclease inhibitor such as aurintricarboxylic acid (ATA) added to the agent. In some embodiments using nucleic acid-based therapeutics, it may also be advantageous to incorporate a signaling peptide onto the construct. Potentially useful peptides include, but are not limited to, nuclear localization signals, endosomal lytic peptides, and transcriptional control elements. These signals can enable improved delivery and/or processing of the therapeutic agents delivered to the cells via EMTAD. This signaling can be accomplished through the use of methods as described in U.S. Pat. No. 6,165,720. While these techniques can be utilized with other delivery systems, the ability of EMTAD to increase the delivery of nucleic acid constructs to target tissues makes it particularly well suited for use with such signals.

Target Tissues

Target tissues well suited for EMTAD include both healthy and diseased cells located in the epidermis, dermis, hypodermis, connective, and muscle tissue. The technique can also be utilized for application in healthy or diseased organs that must be accessed via minimally invasive or other surgical means. Such target tissues include the liver, lungs, heart, blood vessels, lymphatic, brain, kidneys, pancreas, stomach, intestines, colon, bladder, and reproductive organs. One should note that the desired therapeutic effect may be derived from agent delivery to cell types normally located within the target tissues as well as other cell types abnormally found within said tissues (e.g. chemotherapeutic treatment of tumors).

As discussed previously, and depicted in FIG. 1, traditional EMTAD suffers from a lack of precision and reproducibility in the spatial and temporal relationship between the administration of the therapeutic agent and the electrical signal. In contrast to the traditional EMTAD approach, the present invention describes methods and apparatus for combined CTAA and ESA to provide a more advantageous clinical application of EMTAD. This invention utilizes various aspects of CTAA in conjunction with ESA to provide reproducible, consistent, and efficacious therapeutic agent delivery. More specifically, the methods and apparatus proposed herein provide spatial and temporal control over administration of a therapeutic agent relative to the application of electrical signals, thereby improving the movement and/or uptake of said agent in the target tissue.

Methods

In one aspect, the invention described herein provides methods for controlled administration of a therapeutic agent followed by ESA. These methods consist of, but are not limited in scope or sequential relationship to, the determination of treatment parameters, patient preparation procedures, CTAA, ESA, and additional measures.

Determination of Treatment Parameters

Treatment parameters are dictated by the desired dosing of the therapeutic agent. Therapeutic agent dosing may depend on the particular indication or treatment application (such as the type and location of the target tissue), as well as various patient parameters (such as age and body mass). Dosing of the therapeutic agent may be controlled by parameters pertaining to administration of the therapeutic agent and ESA. Controllable parameters pertaining to CTAA include agent volume, agent viscosity, and injection rate. Controllable parameters pertaining to ESA include the characteristics of the electrical signals, the tissue volume exposed to the electrical signals, and the electrode array format. The relative timing and location of CTAA and ESA are parameters providing further control over therapeutic agent dosing.

Patient Preparation

Patient preparation includes, but is not limited to, antiseptic cleansing and anesthetic administration, including local or regional, nerve block, spinal block, epidural block, or general anesthesia. In the case of intramuscular (IM) ESA, protocols to minimize the effects of electrical stimulation of the muscle may be taken, including thermal control (e.g. cooling the muscle), administration of anesthetics, and/or alternative stimulation patterns sufficient for mitigation of discomfort. One should ensure that the selected patient preparation techniques do not adversely affect therapeutic efficacy, if acceptable alternatives exist. For example, it has been shown that certain anesthetics can have an undesirable effect on plasmid DNA-based therapies.

CTAA and ESA

In the practice of the method, the application of CTAA and ESA are combined, enabling consistent and reproducible therapeutic agent delivery. Two representative embodiments of apparatus suitable for CTAA include automatic injection devices and jet injectors.

CTAA Apparatus Embodiments

Figure 2:
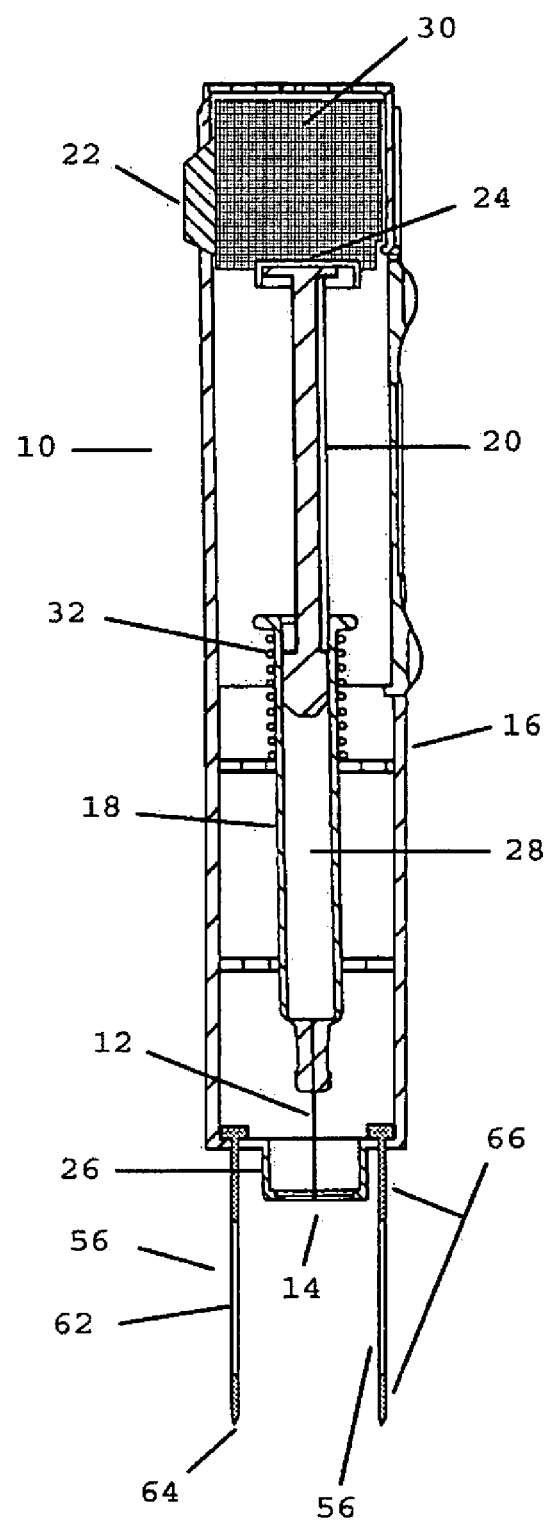
FIG. 2 is a cross sectional depiction of an embodiment of an apparatus of the invention comprising an integrated means for therapeutic agent administration and electrical signal application.

Turning now to the additional drawings, where like elements are identified by like numerals throughout the figures, as depicted in FIG. 2, in certain embodiments an automatic injection device 10 is utilized as the means of controlled administration of therapeutic agents to the target tissue. As used herein, an automatic injection device is a device that is capable of administering a therapeutic agent to a patient at a controlled rate through at least one hollow injection needle 12, such as a hypodermic needle, each with at least one orifice 14.

Conveniently, the automatic injection device 10 will utilize a housing 16 to enclose, for example, a conventional disposable syringe 18, plunger 20 and needle 12 arrangement, together with the means necessary to insert the needle into the patient and dispense the therapeutic agent through the needle (as described below). Administration of therapeutic agents with automatic injection device 10 is initiated by an operator activating trigger 22 and begins with the insertion of injection needle 12 containing one or more orifices 14 through which the therapeutic agent can be transferred into the patient. Descriptions and examples of automatic injection devices which can find use in the present invention are provided in U.S. Pat. Nos. 6,077,247 and 6,159,181, the entire disclosures of which are incorporated by this reference.

Preferably, injection needle 12 is inserted into the patient by a drive mechanism 24 contained within automatic injection device 10. Preferably, injection device 10 also includes depth control means 26 for reliably controlling the depth of penetration of injection needle 12. Once needle 12 is inserted, the therapeutic agent is transferred at a controlled rate from a suitable reservoir 28 through orifice 14 of needle 12 and into the patient. It is also considered desirable to include a means to inhibit relative motion between the plunger and the body of the syringe until such time as the injection needle has reached the predetermined location within the patient, and thereby minimize the distribution of the agent outside of the predetermined area of interest.

The automatic injection device 10 may contain a single injection needle 12 or multiple needles, through which single or multiple types of agents may pass, depending upon the specific application. The energy source 30 utilized to transfer the therapeutic agent from the reservoir 28 into the patient is commonly compressed gas or a spring, though other sources may be utilized.

Given that multiple applications for the present invention are contemplated and that there are significant differences in body and tissue composition between patients, it is likely that reproducible and consistent practice of the invention in a large patient population will desirably include a means for adjusting the injection parameters. Such injection parameters include the needle size, injectant viscosity, injectant volume, concentration of therapeutics, and injection rate. A means for adjusting these parameters is desirable to compensate for various characteristics of the therapy recipient, including age, weight, dosing, target tissue type, and the target tissue depth, especially for transcutaneous administration (which may be affected, among other factors, by the recipient's age and level of obesity).

In certain indications, a single-use and/or self-destructing needle-syringe may be used as therapeutic agent reservoir 28, thereby preventing cross-contamination of blood-borne pathogens between recipients. Similarly, protection is provided to the operator against accidental needle-stick injuries and resulting blood-borne pathogen transmission by using automatic injection devices that incorporate a means of needle retraction 32 after use. This method of agent administration is particularly useful in high-risk situations, such as injecting patients infected with HIV, Hepatitis, or any other blood-borne pathogens.

In one specific application of such an embodiment, an automatic injection device is used for IM injection of plasmid DNA encoding for a therapeutic protein. Skeletal muscle has several characteristics that make it a desirable target tissue for this application. First, skeletal muscle constitutes up to 40% of the average adult's body mass and is easily accessible for transcutaneous administration of the plasmid. In addition, muscle cells rarely divide in vivo and thus, the introduced plasmid will not be lost during mitosis. Muscle cells are also multi-nucleated, thereby providing multiple targets for the plasmid once it reaches the intracellular space. These characteristics enable prolonged expression and secretion of the protein into systemic circulation. If the gene of interest can be transfected into an adequate number of muscle fibers, the tissue can produce the protein at levels sufficient to induce a biologic effect in patients. For example, an anemic patient may receive an IM injection of plasmid DNA encoding for the protein erythropoietin (EPO), followed by electroporation. Upon treatment, transfected cells would produce and secrete the EPO protein, leading to an increase in hematocrit. The benefits of having such a treatment, which allows the body to manufacture its own EPO, are very enticing. By introducing and expressing EPO in muscle using electroporation, the body would be able to produce EPO for an extended period of time and patients may require boosters at substantially reduced time intervals.

Figure 3:
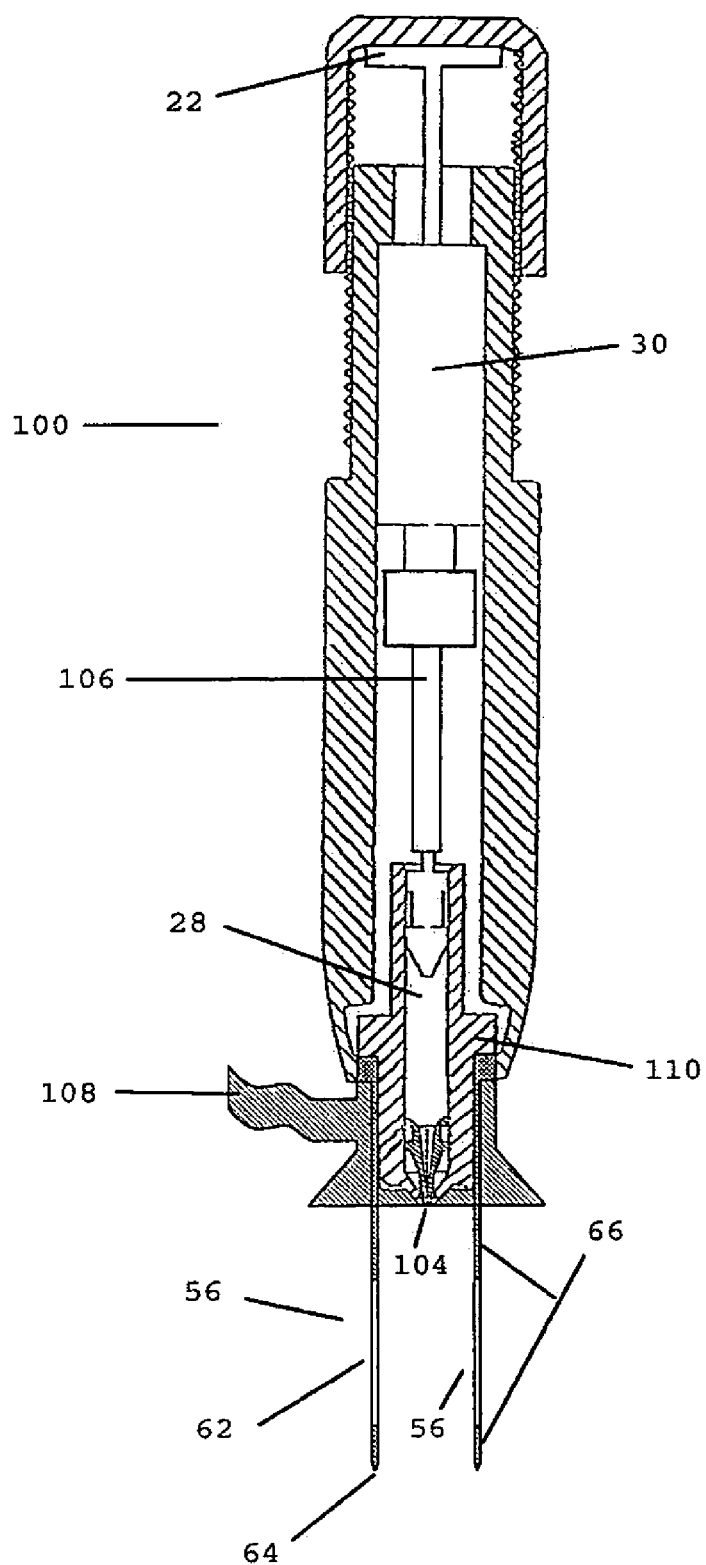
FIG. 3 is a cross sectional depiction of an alternative embodiment of an apparatus of the invention comprising an integrated means for therapeutic agent administration and electrical signal application.
Figure 4:
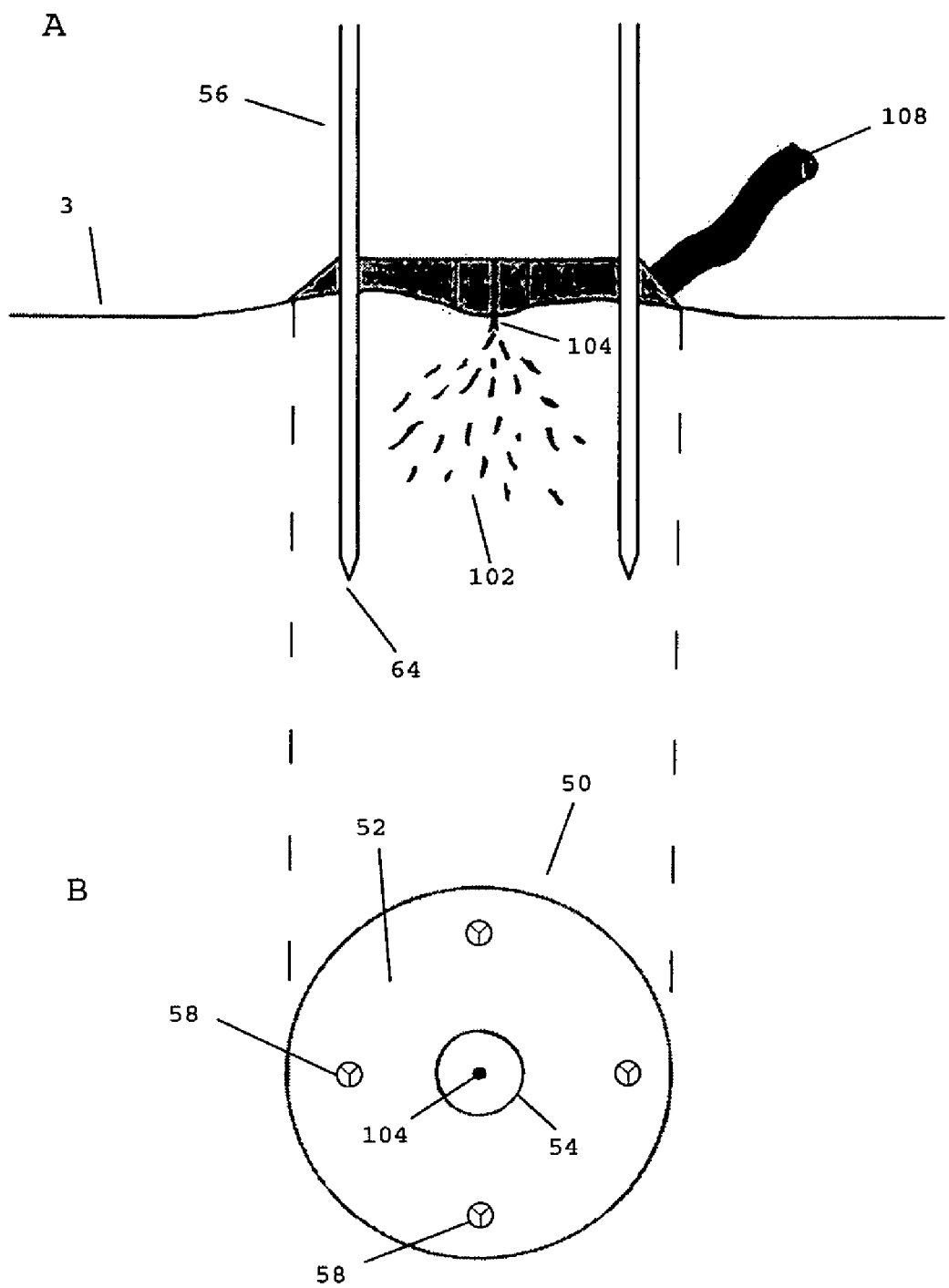
FIG. 4A is a cross sectional view of a portion of an embodiment of the invention during therapeutic agent administration.
FIG. 4B is a bottom view of the embodiment of FIG. 4A, depicting the portion of the device which interfaces with the tissue of a patient.

In other embodiments of the present apparatus, as depicted in FIGS. 3 and 4, a jet injector 100 is utilized as the means for CTAA to the target tissue. Examples of jet injection devices include: WIPO Publication Nos. WO0113975, WO0113977, and WO0009186. Similar to the use of an automatic injection device, administration of therapeutic agents with a jet injector 100 is initiated by an operator activating trigger 22 but transmission of the agent from a jet injector to the patient relies on the penetration of a high-pressure stream 102 of such agent through an orifice 104 into the tissue. Although jet injection is typically accomplished without the use of a penetrating injection needle, in some cases the injection orifice 104 is located at the terminal end of a mini-needle used to bypass the outermost layers of a tissue system. The high-pressure stream 102 of therapeutic agent generated by jet injector 100 then follows the path of least resistance as it is forced through the tissue, resulting in a widely dispersed distribution of the therapeutic agent (see FIG. 4A). The jet injector 100 may contain a single orifice 104 or multiple orifices for injection, through which single or multiple types of agents may be transferred, depending upon the specific application. The source of energy 30 used to activate a plunger 106 to transfer the therapeutic agent from a suitable reservoir 28 through the injection orifice 104 is commonly compressed gas or a spring, but other energy sources can also be used.

In order to achieve reproducible and consistent agent administration, where the population is expected to exhibit variable patient parameters, the orifice size and shape, injectant pressure, injectant viscosity, injectant volume, concentration of therapeutics, and injection rate are a few examples of the adjustable jet injection parameters which can be controlled. Such adjustable parameters of the jet injector are necessary to account for various characteristics of the therapy recipient, including age, weight, dosing, target tissue type, and the target tissue depth, especially for transcutaneous administration (which may be affected, among other factors, by the recipient's age and level of obesity). Such adjustable parameters may also be necessary to ensure that the agent is stable and viable when exposed to the pressure and shearing stress inherent to jet injection-mediated administration.

In the case of transcutaneous injection, the interface between the injector orifice and skin is also critical in achieving reproducible and safe administration; the spatial location of the jet injector should be maintained for the duration of injection. To address this issue, in certain embodiments the jet injector can be provided with the means of maintaining a slight vacuum 108 at the device/tissue interface to facilitate administration of the technique and stabilize the spatial location of the unit. Interface stabilization may also be accomplished with the use of adhesives, with the temporary application of restraint mechanisms, or any combination thereof.

A significant concern with jet injection technology is ballistic contamination, in which the jet injection builds pressure in the tissue that is greater than the pressure in the injector, causing a small backflow of blood or other bodily fluids onto the device. In response to this problem, a single-use, self-destructing vial 110 may be used for therapeutic agent containment of the jet injector. This prevents cross-contamination of blood-borne pathogens between recipients. Similarly, since most jet injectors have no needle, protection is provided to the operator against accidental needle-stick injuries and resulting blood-borne pathogen transmission. Such a form of needleless injection is particularly useful in high-risk situations, such as injecting patients infected with HIV, Hepatitis, or any other blood-borne pathogens.

ESA Parameters

One representaive form of ESA is electroporation, but all forms of ESA share certain common features desirable for the efficient application of the techniques to EMTAD. A critical aspect of electroporation is the generation and propagation of electroporation-inducing electrical fields within the region of tissue targeted for therapeutic agent delivery. There are several methods for generating such fields in vivo, including surface and penetrating electrode arrays. The present invention can be practiced with any electrode system suitable for propagating the electrical signals within the targeted region of tissue. The specific characteristics of the electrode systems will determine if that type of electrode is suitable for use in a given application.

With surface style electrode arrays, an electrical field is propagated through the surface of the skin and into the target tissue. Unfortunately, surface style electrode arrays, such as plates or meander-type electrodes (as described in U.S. Pat.

No. 5,968,006), are inefficient or impractical for most indications. The electrodes are typically unable to target regions beyond the most superficial tissues, they cannot be applied in a reliable fashion, and their use often can result in burning and scarring at the site of application.

Penetrating electrodes are typically more desirable for most forms of ESA, and particularly for electroporation. Penetrating electrodes are defined as conductive elements whose size and shape are sufficient to enable insertion through the matter covering a tissue of interest, such as skin covering muscle tissue, or the outer layer(s) of such tissue. There are numerous embodiments of penetrating electrode array systems, including bipolar and multielement electrode arrays. The simplest penetrating electrode array is the bipolar system, which consists of two penetrating electrodes connected to the opposite poles of a pulse generator. Systems of penetrating bipolar electrodes have been used extensively in preclinical studies of electroporation. However, the non-uniform electrical fields characteristic of bipolar electrodes makes them an inefficient means for generating threshold levels sufficient for electroporation throughout a target region of tissue. More complex systems have been developed using three or more electrodes to comprise a multielement array. The specific geometrical arrangement and activation pattern of these multi-element arrays can result in superior performance characteristics compared to the bipolar approach.

For many clinical indications, a grid-based multielement electrode array, such as the TriGrid™ electrode system, is the most advantageous means of applying ESA in accomplishing the therapeutic objective. The TriGrid™ system, disclosed in U.S. Pat. No. 5,873,849 (the entire disclosure of which is incorporated herein by reference), consists of slender penetrating electrodes with a geometry and activation pattern designed to maximize field uniformity within a targeted volume of tissue. As a result, the ESA effect can be achieved throughout the target volume with minimized variability due to the electrical fields propagated within the tissue.

The TriGrid™ design considerations ensure that the threshold field strengths required to achieve electroporation are propagated throughout the target tissue while minimizing the amount of tissue exposed to excessively high fields that could result in tissue injury. These more uniform electric field distributions are achieved by simultaneously activating more than two of the electrodes within the array, thereby reinforcing the electric fields being propagated in the more central tissues away from the electrodes. Since the probability of achieving membrane permeability can also depend on the physical dimensions and orientation of the cell, the sequential propagation of electrical fields at different angles increases the likelihood that the electroporation effect can be achieved in any given cell.

Figure 5:
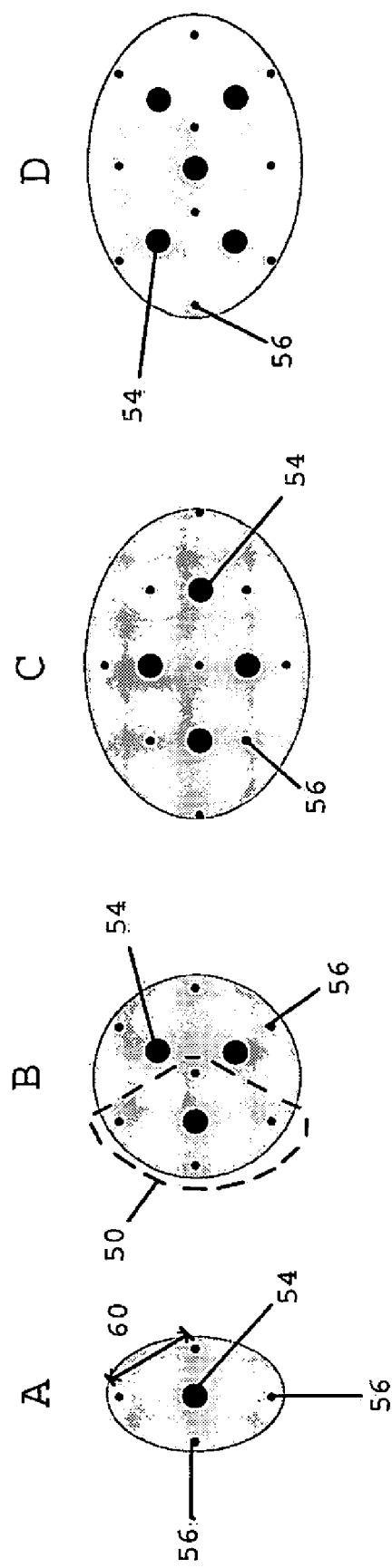
FIGS. 5A–D illustrate several embodiments of embodiments of the invention depicting the portion of the apparatus that interfaces with the tissue of a patient.
Figure 6:
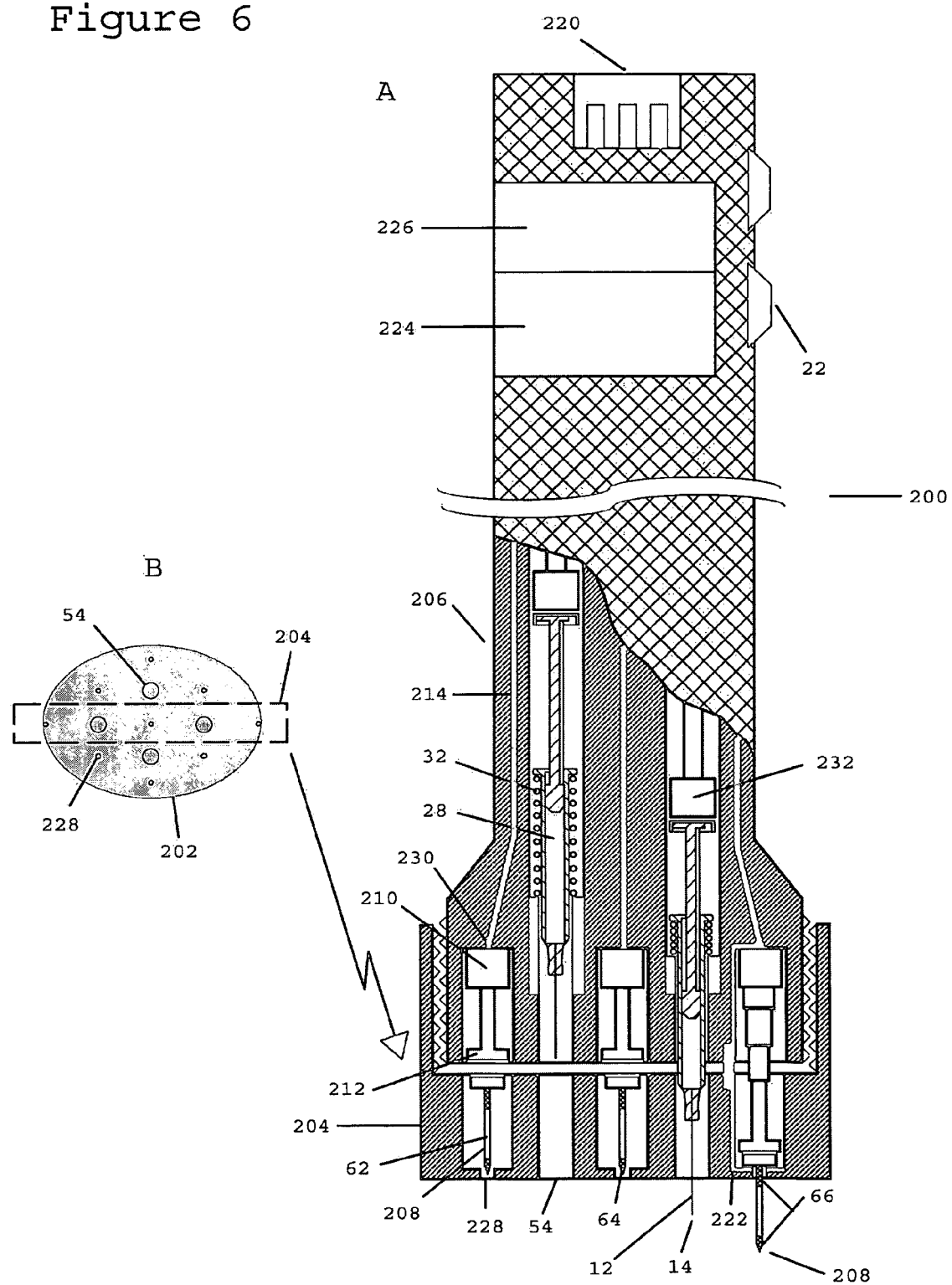
FIG. 6A is a partial cross sectional view of a further alternative embodiment of an apparatus of the invention comprising an integrated means for therapeutic agent administration and electrical signal application.
FIG. 6B is a bottom plan view of the embodiment of FIG. 6A, depicting the portion of the device which interfaces with the tissue of a patient.

As depicted in FIG. 5, each set of four electrodes establishing a generally diamond shaped multielement array is called a Unit TriGrid™ 50. Any number of Unit TriGrid™ "modules" can be integrated together and expanded to form electrode arrays with different geometries capable of treating various shapes and volumes of tissue. Several important clinical benefits are derived from the use of the expandable TriGrid™ electrode array system. First, the system allows the patient to be treated with a single placement of the electrodes, thereby minimizing the time required for the procedure and reducing any discomfort associated with repeated penetration and stimulation of an electrode array. Second, by controlling the amount of tissue exposed to the ESA-induced electrical fields, the grid based electrode format essentially provides a method for accurately adjusting the dose of the therapeutic agent. Finally the TriGrid™ is likely to result in consistent application of the treatment from patient-to-patient and operator-to-operator since it reduces uncertainty associated with the amount of tissue targeted by threshold level electroporation-inducing electrical fields.

In certain preferred embodiments, a TriGrid™ array is utilized as the mode of establishing electroporation-inducing electrical fields. A high voltage electrical state sequencer and electrical signal generator is connected to each of the electrodes through conductive cables, thus generating an electroporation-inducing electrical field. In order to achieve reproducible and consistent therapeutic efficacy provided variable patient parameters, the electrode size, shape, and surface area, the electrical field strength (typically 50–2000 volts per centimeter), the frequency of stimulation (typically 0.1 Hertz to 1 megahertz), the waveform (such as bipolar, monopolar, AC, capacitive discharge, square, sawtooth, or any combination thereof) and the electrical signal duration (typically 1 microsecond to 100 milliseconds) are a few examples of the adjustable electroporation-inducing electrical field parameters. Selection of such adjustable electroporation parameters is based, among other factors, on the agent to be delivered, the dosing, the specific application and method of administration, the type and location of the target tissue, and the volume to be treated. In other embodiments, plate electrodes, bipolar, and other multielement electrode arrays may be utilized as the mode of generating electroporation-inducing electrical fields; however, the TriGrid™ array is superior in accomplishing the therapeutic objective for most indications.

Additional Procedures

There are several additional procedures that may be included in the application of CTAA and ESA, which assist in the accomplishment of the desired therapeutic objective. For instance, after the therapeutic agent has been administered it may be advantageous to utilize techniques to enhance agent distribution within the tissue by molecular movement. Suitable techniques to enhance molecular movement and homogeneity include iontophoresis, electroosmosis, ultrasound, and thermal means. In the case of iontophoresis and electroosmosis, it may be desirable to use the same electrodes that deliver electroporation; however, additional electrodes may be used. The administration of dexamethasone and poloxamer, among other agents that can affect the state of the cell membrane, have been shown to enhance various aspects of electroporation therapy. Following treatment, precautionary measures may be taken to cleanse the treatment site.

Integrated CTAA/ESA Apparatus

There are several embodiments suitable for achieving spatially and temporally controlled TAA relative to application of electrical signals. A preferred embodiment providing spatial and temporal control is an apparatus wherein therapeutic agent administration and ESA are accomplished by means of an integrated unit. The integrated unit may utilize administration means such as an automatic injection device (FIG. 2) or a jet injector device (FIG. 3) as the mode of CTAA, with electroporation-inducing electrical fields as the mode of ESA. Such an embodiment does not limit this invention of combined employment of CTAA and electroporation to an integrated unit, or by said means. However, integration of such an apparatus provides improved temporal and spatial control that may not be as accurately achieved with application of individual CTAA and electroporation units.

Embodiments

The appropriate temporal and spatial generation of an electroporation-inducing electrical field with respect to the timing and location of the therapeutic agent administration is critical for achievement of consistent and reproducible therapeutic effects. For instance, if the operator administers a therapeutic agent with one device, and then employs another device for establishment of an electroporation-inducing electrical field, there may be variability in the relative temporal and spatial applications of CTAA and electroporation. Such inter-patient variability, due to inter-operator variability, can result in highly undesirable therapeutic inconsistencies. In the practice of the proposed integrated unit, operator training and variability are significantly reduced, since the spatial and temporal relationship of the CTAA and electroporation are controlled through the use of an integrated application system and control means rather than the operator. Furthermore, operator error by inconsistent and inaccurate temporal and spatial establishment of the electroporation-inducing electrical field relative to the therapeutic agent administration may be minimized, enabling reproducible and consistent therapeutic efficacy and dosing.

In all embodiments, administration of the therapeutic agent is performed in a spatially and temporally controlled fashion relative to ESA. Accordingly, spatial control and temporal control are both addressed below as separate aspects. Though addressed separately, these aspects may be combined in all such embodiments to form an integrated application unit providing both spatial and temporal control over administration of the therapeutic agent. The particular combination of embodiments employed is dictated by the specific indication.

Embodiments Providing Temporal Control

In the combination of therapeutic agent application and electroporation, the need for temporal control is twofold: 1) the ability to administer the therapeutic agent at a controlled rate, and 2) the ability to control the sequence and timing of TAA and electroporation application. In the present invention, the former issue is addressed by the use of an automated injection apparatus, and the latter is addressed by integrating this automated injection apparatus with an appropriate means for the application of electroporation.

The rate of therapeutic agent administration into the tissue is largely controlled by the design of the administration apparatus. Two common administration methods that provide suitable control over the rate of agent administration are automatic injection devices 10 and jet injector devices 100. For both administration methods, an energy source 30 is required to transfer the therapeutic agent from a suitable reservoir 28 in the device through an orifice 14, 104 and into a target region of tissue at a controlled rate. Suitable sources of energy for automatic injection devices and jet injectors include springs, compressed gas, and electromechanical means. The rate of administration may be controlled by regulation of several parameters, including the energy source (e.g. spring constant, gas pressure, voltage, or current), needle diameter, orifice diameter, and agent viscosity. The parameters may be selected by the operator prior to administration to set the desired rate. However, once administration is initiated, the rate is operator-independent, and the agent is transferred at a predetermined rate.

In the practice of the present invention, an integrated unit is applied to the therapy recipient, allowing the desired sequence and timing of CTAA and electroporation to be achieved in a controlled and reliable fashion without undesirable time delays and/or multiple device placements. For example, one treatment protocol calls for the administration of plasmid DNA encoding for a therapeutic protein, followed by generation of an electroporation-inducing electrical field, and then followed by administration of dexamethasone. In the absence of the present invention, there would be three different device placements, with an unavoidable time interval in between the operator's placement and activation of each device. This complexity increases the probability that inter-patient variability would arise from inconsistent temporal application of each device by individual operators who are likely to have substantially different skill levels. This complexity and variability is compounded in the case where multiple application sites are necessary to get adequate dispersal of the agent to a treatment region within the target tissue. Using the described invention, however, only a single device is required, enabling any desired sequence of CTAA, electroporation, and additional procedures to be applied with minimal spatial and temporal variability and limitations. This feature is critical for agents that must reach the interior of the target cells to maintain efficacy. The treatment may not be consistently and reliably accomplished with multiple units, where temporal limitations and injection rate variability may be present in the treatment regimen. For example, when plasmid DNA is exposed after in vivo administration to the extracellular environment, physiological enzymes (DNases) break it down. Since the exact rate of enzymatic activity is dependent on the specific patient, minimizing the time interval between CTAA and electroporation allows more accurate control over the treatment dosage. In the in vivo environment, viability must be maintained by expeditious entry of the therapeutic agent to the interior of the target cells, and this may not be as consistently and reliably achieved with multiple units as it may be with an integrated unit, with which time lags are not a significant limitation and enzymatic activity is reduced as a source of variability.

Embodiments Providing Spatial Control

There are several embodiments suitable for achieving spatially controlled therapeutic agent administration. One embodiment suitable for spatially controlled therapeutic agent administration is a template 52, as depicted in FIGS. 5A–D, containing a single (FIG. 5A) or a plurality (FIGS. 5B–D) of ports 54 designed to accommodate injection orifices characteristic of a jet injector or automatic injection device at a fixed location relative to electrodes 56 suitable for generation of electroporation-inducing electrical fields. Additionally, the use of ports 54 provides improved angular and depth control over administration of the therapeutic agent. The template 52 may contain a single or plurality of port interlocks for administration device stabilization, through which any combination of automatic injection devices or jet injectors may be connected and employed in a spatially controlled fashion.

A preferred embodiment of the invention that provides spatial and temporal control in the delivery of therapeutic agents is an apparatus wherein CTAA and ESA are accomplished by means of an integrated unit. The integrated unit may utilize administration methods such as an automatic injection device or a jet injector as the mode of CTAA, with electroporation-inducing electrical fields as the preferred mode of ESA. There may also be indications for which any combination of single or multiple automatic injection devices and jet injectors is beneficial. For instance, the TriGrid™ electrode array allows for virtually all target tissue volumes and shapes to be treated with a single placement of the array. A device with multiple agent administration means would then allow for reproducibly co-localized CTAA and electroporation to a wide variety of target tissues with a single placement of the integrated unit. The number of administration means implemented with respect to the number of Unit TriGrid™ arrays may depend on various treatment parameters, including the nature of the agent to be delivered, the desired dosing, the type and location of the target tissue, and the volume to be treated.

In the practice of the invention utilizing such embodiments, the integrated unit is placed in the desired location, the administration device is employed to administer the therapeutic agent, and the electrode array of electrodes is activated in the target tissue, all without spatial relocation of the integrated unit. Desirably, the electrode array can be provided with the means to adjust the spatial relationship to the orifice, for example, by providing retractable electrodes. In such an embodiment, the electrodes would then be deployed upon command, and activated at the appropriate time, in order to effect the EMTAD treatment. The electroporation-inducing electrical field is thereby established, enabling delivery of the therapeutic agent to the interior of the target cells, and the electrode array is then retracted from the target tissue. This single-placement device minimizes spatial variability and limitations on the sequential application of CTAA and electroporation, while enabling highly accurate control over spatial parameters, such as the application of CTAA relative to electroporation. This is especially important for electroporation, where reproducible co-localization between the therapeutic agent and the target tissue is optimal for therapeutic agent delivery in consistent, efficacious therapies.

In all embodiments described above, additional distributional control is derived from combination of rate control with a template-based device, or as a component of an integrated unit. For example, if a plurality of administration devices is used, then the spatial and temporal relationship between location and timing of injections is readily controlled, thereby providing a more consistent, rapid, and homogeneous distribution of the therapeutic agent.

Description of an Exemplary Integrated Unit Embodiment

As depicted in FIGS. 2, 3, 6 and 7, the integrated unit may use an automatic injection device 10, jet injector 100, or any combination thereof as the mode of CTAA. For certain indications, an automatic injection device 10 may be the preferred mode of CTAA. The automatic injection device may use standard syringes and needles, fixed or non-fixed. A disposable, self-destructible, and/or pre-filled needle-syringe unit 18 may be preferable for certain indications. The needle should be positioned within a housing 16 that incorporates a penetration-depth controlling means 26, thereby preventing accidental needle stick. For added safety, the automatic injection device may provide retraction of the needle once insertion and injection has been completed. Accidental discharge prevention means may also be desirable. For other indications, a needleless or mini-needle jet injector 100 may be the preferred mode of CTAA. A disposable, self-destructible, and/or pre-filled vial 110 containing the agent may be preferable for certain indications. If the jet injector contains a mini-needle, as may be the case for transcutaneous penetration, the mini-needle should be positioned to prevent accidental needle stick. Likewise, the jet injector may provide retraction of the mini-needle once insertion and injection has been completed. It may also be desirable to have accidental discharge prevention means. For all administration devices containing needles and mini-needles, it may be desirable to have the deployed or retracted state of said needles and mini-needles displayed to the operator.

The integrated unit may use the TriGrid™ array as the mode of implementing ESA, with elongate electrodes 56 disposed according to the tissue shape and volume to be treated. In one embodiment of the invention, an integrated apparatus 200, shown in FIGS. 6 and 7, includes an array of electrodes 202 contained within a separable, and optionally disposable, sub-assembly 204 that can be easily attached to and removed from the main unit 206, allowing for controlled-usage and disposable electrodes. As described above, certain embodiments of the invention employ retractable electrodes 208, as it is preferable if the electrodes can be contained within the apparatus 200 prior to their deployment into the target tissue. In cases of transcutaneous application, retractable electrodes would allow for improved operator safety, reduced risk of a loss in electrode sterility prior to insertion and mitigation of any belonephobia for the patient. Control over movement of such electrodes may be provided by spring, compressed gas, or other appropriate energy source 210 in conjunction with a drive mechanism 212 to extend the electrodes 208 through port 228 and into the patient. The electrodes 208 may be actuated individually or as a unit, and preferably, the deployed or retracted state of the electrodes is displayed, either individually or as a unit, to the operator. As with automatic and jet injection devices, the use of retractable needle-type electrodes 208 may reduce belonephobia experienced by the therapy recipient, while providing the operator with increased safety to blood borne pathogens and other needle-stick related injury.

Electrical continuity is necessary between the desirably active electrodes and the electrical signal generator. Therefore, in embodiments where the electrode array is detachable, a continuous and reliable electrical connection 214 should be readily achieved between the electrodes 208 within the array 202 and the apparatus 200. The invention also includes an electrical signal generating means 216 in conductive communication with the apparatus 200. The nature of the electrical signal generating means 216 will depend on the desired application. In some embodiments, the electrical signal generating means 216 can be located 226 within the integrated apparatus 200. Desirably, in such an embodiment the connections necessary to maintain electrical continuity between the electrodes and the electrical signal generator are housed internal to the apparatus. In the case of external electrical signal generating means 216, as depicted in FIG. 7, a cable 218 between the generator 216 and the apparatus 200 is provided with a suitable connector 220 located on the apparatus 200 in a manner to minimize interference with operator use. As electrodes 208 may be retracted or deployed, conductive housing 222 is provided for electrical connection between deployed electrodes and the electrical signal generator 216. Conductivity may also be accomplished by connection 230 through the electrode drive mechanism 212 and/or energy source 210.

Selection of electrode parameters is a critical component of electroporation therapy. Electrode parameters include diameter, tip profile, length, conductivity, and materials. The electrodes may be hollow, allowing for the administration of anesthetics or other agents. The electrodes may also be coated with anesthetics and/or lubricious agents for pain mitigation and ease of insertion. The electrode parameter selection is dictated by several treatment factors, including properties of the target tissue, tissue volume to be treated, and charge injection/current densities at the electrode-tissue interface. For example, in the transcutaneous application of electroporation, trocar tip 58 (polyhedron with three faces) electrodes with a nominal diameter of 0.005" to 0.05" are desirable. The inter-electrode spacing 60 and penetration depth define the volume of tissue to be treated. For electroporation in healthy tissues, it is often desirable that the electrodes have a sufficiently inert surface material 62 which is electrochemically stable and will not exhibit substantial oxidation-reduction reactions with the interstitial environment when exposed to high charge injections that may occur as a result of ESA. Such surfaces may be platinum, platinum-iridium, iridium, iridium-oxide, gold, and titanium nitride. Depending upon the material chosen, it may be desirable for cost and structural reasons to deposit these inert metals to the surface of a base metal. Appropriate base metals include, but are not limited to titanium, tungsten, stainless steel, and MP35N.

The process of deposition for the desired electrochemically stable coating may consist of chemical or physical vapor deposition, creating coatings on the order of tenths to hundreds of microns. The level of charge injection and irreversible oxidation-reduction reactions should be considered when choosing a sufficiently inert material and deposition thickness. In order to target the ESA electrical fields to a specified region, including elimination of non-homogeneous electrical fields from the electrode tips 64, dielectric coatings 66 such as Polytetrafluoroethylene (PTFE), Parylene, and Silicon Carbide may be deposited onto the electrode at thicknesses of tenths to hundreds of microns. The pinhole size and dielectric strength of such coatings should be considered when choosing an appropriate dielectric material and thickness.

A further aspect of the invention provides a system wherein the sequential timing and functions of the integrated CTAA-ESA unit are controllable. This may provide, for example, presettable procedure parameters, procedure automation, and/or closed loop systemic control. The control system 224 of the integrated unit may regulate parameters pertaining individually to CTAA and electroporation, and collectively to their integrated function. In certain embodiments, the control system may regulate the effective administration and dosing of therapeutic agents by adjustment of CTAA and electroporation parameters. Other treatment parameters to be controlled include application of a local anesthetic, placement and removal of retractable electrodes, administration of additional therapeutics, and the timing and duration of each step of the procedure.

In certain embodiments, the control system and means for electrical signal generation are incorporated into a portable or handheld unit for use with the integrated CTAA-ESA apparatus. For portability, a spring or compressed gas may be used as an energy source 30 acting through a drive mechanism 232 as a means of therapeutic agent transfer, and desirably having multiple settings for operator-selectable control over the rate of transfer in therapeutic agent administration. If a spring is used, then the loaded and unloaded state of the spring could be displayed to the operator. If compressed gas is used, a qualitative or quantitative pressure level could be displayed to the operator. In this embodiment, the integrated unit may be powered by battery, capacitor bank, or pulse forming network that is energized by use of a portable station, solar cells, or other electrical sources.

All patents and patent applications cited in this specification are hereby incorporated by reference as if they had been specifically and individually indicated to be incorporated by reference.

Although the foregoing invention has been described in some detail by way of illustration and Example for purposes of clarity and understanding, it will be apparent to those of ordinary skill in the art in light of the disclosure that certain changes and modifications may be made thereto without departing from the spirit or scope of the appended claims.

What is claimed is:

1. An apparatus for the intracellular delivery of a therapeutic agent to a predetermined site within the tissue of a patient comprising:

means for the administration of said therapeutic agent to said patient comprising a reservoir for the therapeutic agent, at least one orifice through which the agent is administered, and an inanimate source of energy sufficient to transfer a predetermined amount of the therapeutic agent from said reservoir through said orifice to the predetermined site within the tissue of the patient;

a plurality of penetrating electrodes arranged with a predetermined spatial relationship relative to said orifice; and means configured for generating an electrical field which facilitates the intracellular delivery of said therapeutic agent said means operatively connected to said electrodes.

2. The apparatus as recited in claim 1 wherein the electrodes comprise a subassembly that can be separated from the orifice.

3. The apparatus as recited in claim 1 further comprising means for adjusting the predetermined spatial relationship between said electrodes and said orifice.

4. The apparatus as recited in claim 3 wherein said means for adjusting the spatial relationship comprises a source of energy.

5. The apparatus as recited in claim 1 wherein the electrodes comprise a conductive, electrochemically stable compound.

6. The apparatus as recited in claim 1 wherein the electrodes comprise a conductive metal coated with a conductive, electrochemically stable compound.

7. The apparatus as recited in claim 5 wherein said conductive, electrochemically stable compound consists of at least one of the following materials: titanium nitride, platinum, platinum iridium, iridium oxide.

8. The apparatus as recited in claim 1 wherein the means for administration of the therapeutic agent is a jet injector.

9. The apparatus as recited in claim 8 wherein the source of energy to transfer the therapeutic agent is at least one compressed gas.

10. The apparatus as recited in claim 8 wherein the source of energy to transfer the therapeutic agent is at least one spring.

11. The apparatus as recited in claim 8 wherein the jet injector comprises means for controlling the rate at which the agent is transferred through the orifice.

12. The apparatus as recited in claim 1 wherein the means for administration of the therapeutic agent is an automatic injection device.

13. The apparatus as recited in claim 12 wherein said reservoir is a syringe including a penetrating hypodermic needle.

14. The apparatus as recited in claim 12 wherein the source of energy to transfer the therapeutic agent is at least one compressed gas.

15. The apparatus as recited in claim 12 wherein the source of energy to transfer the therapeutic agent is at least one spring.

16. The apparatus as recited in claim 13 wherein the automatic injection device comprises means for controlling the depth of penetration of said needle into the patient.

17. The apparatus as recited in claim 12 wherein the automatic injection device comprises means for controlling the rate at which the agent is transferred through the orifice.

18. The apparatus as recited in claim 6 wherein said conductive, electrochemically stable compound consists of at least one of the following materials: titanium nitride, platinum, platinum iridium, iridium oxide.

19. The apparatus as recited in claim 1 wherein the means for generating an electrical field is configured to induce an electrical field of from approximately 50 to approximately 300 V/cm between at least two of said electrodes.

20. The apparatus as recited in claim 1 wherein die means for generating an electrical field is configured to deliver a signal for a duration of from approximately 1 microsecond to approximately 100 milliseconds and at a frequency of from approximately 0.1 Hertz to approximately 1 megahertz to at least two of said electrodes.

\* \* \* \* \*